(12) United States Patent
Tanaka et al.

(10) Patent No.: US 9,277,747 B2
(45) Date of Patent: Mar. 8, 2016

(54) AGRICULTURAL COMPOSITION COMPRISING PH SENSITIVE AGRICULTURAL CHEMICALS AND ORGANIC PH BUFFER

(75) Inventors: Kelly S. E. Tanaka, Toronto (CA); Martin David Bloomberg, Toronto (CA)

(73) Assignee: NUTRIAG LTD., Toronto, Ontario (CA)

( * ) Notice: Subject to any disclaimer, the term of this patent is extended or adjusted under 35 U.S.C. 154(b) by 0 days.

(21) Appl. No.: 13/191,988

(22) Filed: Jul. 27, 2011

(65) Prior Publication Data

US 2012/0157317 A1    Jun. 21, 2012

(30) Foreign Application Priority Data

Dec. 21, 2010   (CA) ..................................... 2726064

(51) Int. Cl.
| | | |
|---|---|---|
| A01N 25/02 | (2006.01) | |
| A01N 25/00 | (2006.01) | |
| A01N 25/22 | (2006.01) | |

(52) U.S. Cl.
CPC ................ *A01N 25/02* (2013.01); *A01N 25/22* (2013.01)

(58) Field of Classification Search
CPC .......... A01N 25/02; A01N 25/22; G06T 9/00; H04N 19/105; H04N 19/119; H04N 19/136; H04N 19/176; H04N 19/96
USPC ........................... 504/358, 362; 514/334, 359
See application file for complete search history.

(56) References Cited

U.S. PATENT DOCUMENTS

| | | | | |
|---|---|---|---|---|
| 4,062,649 | A |  | 12/1977 | Kuderna et al. |
| 5,278,132 | A | * | 1/1994 | Fisher et al. ................... 504/124 |
| 5,514,639 | A | * | 5/1996 | Fisher et al. ................... 504/362 |
| 6,391,262 | B1 |  | 5/2002 | Brinton et al. |
| 2005/0191326 | A1 |  | 9/2005 | Melker |
| 2007/0010400 | A1 | * | 1/2007 | Sabnis et al. ................ 504/116.1 |
| 2008/0227856 | A1 |  | 9/2008 | Melker |
| 2008/0280373 | A1 |  | 11/2008 | Chen et al. |
| 2009/0011516 | A1 |  | 1/2009 | Loussaert et al. |
| 2010/0047176 | A1 |  | 2/2010 | Ravn |
| 2010/0120619 | A1 | * | 5/2010 | Greyling et al. ............... 504/188 |
| 2010/0150842 | A1 |  | 6/2010 | Ravn et al. |

FOREIGN PATENT DOCUMENTS

| | | |
|---|---|---|
| CA | 2495567 | 3/2004 |
| CA | 2536808 | 3/2005 |
| WO | 99/25189 | 5/1999 |
| WO | WO 9925189 A1 * | 5/1999 |

OTHER PUBLICATIONS

Office Action dated Aug. 15, 2012, for Canadian Patent Application No. 2,726,064.
International Search Report for corresponding International Patent Application No. PCT/CA2011/050791 dated Jan. 19, 2012.
Written Opinion for corresponding International Patent Application No. PCT/CA2011/050791 dated Jan. 19, 2012.
"Isolation of the 1,4- and the 6,3-Lactones of D-Glucaric Acid", Bose, et al., Journal of Organic Chemistry, 1961, 5 26 (4), pp. 1300-1301.
Supplementary European Search Report dated Apr. 22, 2014, for European Patent Application No. 11850693.0.

\* cited by examiner

*Primary Examiner* — Janet Epps-Smith
*Assistant Examiner* — Courtney Brown
(74) *Attorney, Agent, or Firm* — Bereskin & Parr LLP/S.E.N.C.R.L., s.r.l.; Patricia Folkins

(57) ABSTRACT

The invention provides a composition in concentrated form ("the concentrate") for dilution with water in the preparation of an agricultural composition for application to crops, soil or animals, comprising a carbohydrate-based pH modifying agent and a pH indicator. The agricultural composition comprises an agricultural chemical whose agricultural activity varies with the pH of the water. The proportions of the pH indicator and the pH modifying agent in the concentrate are selected so that when the concentrate is diluted with an appropriate amount of water, the pH indicator indicates visually by coloration of the composition, whether or not the pH of the water is suitable for acceptable agricultural activity of the chemical. The invention also provides a process for preparing the agricultural composition by mixing the concentrate with water, and adding the agricultural chemical to the composition, if it is not already present in the concentrate.

15 Claims, No Drawings

AGRICULTURAL COMPOSITION COMPRISING PH SENSITIVE AGRICULTURAL CHEMICALS AND ORGANIC PH BUFFER

FIELD OF THE INVENTION

The present invention relates to a composition for agricultural use, wherein the composition comprises one or more pH sensitive agricultural chemicals and a concentrate comprising a pH modifying agent comprising a carbohydrate acid, a pH indicator and optionally one or more pH sensitive agricultural chemicals, wherein the concentrate may be diluted with water, in preparation of the agricultural composition for application to crops, soil or animals.

BACKGROUND OF THE INVENTION

Agricultural chemicals such as fertilizers, pesticides, and herbicides, are typically applied to plant crops, soil and/or animals as an aqueous solution. Many agricultural chemicals have an activity that varies with the pH of the solution, in that they may be sensitive to degradation in solutions that are too alkaline or too acidic. Such agricultural chemicals commonly have an optimum agricultural activity in aqueous solutions having a slightly acidic pH range, for example pH 4-6.

When such agricultural chemicals are used in areas where the water supply has a pH unsuitable for the agricultural chemical in question (for example, "hard" waters which may be alkaline), the user or operator typically modifies the pH of the water whereby the agricultural chemical is diluted, so that the water is in an acceptable and preferably optimum pH range to ensure optimum or at least acceptable agricultural activity of the chemical in question. This is effected by adding to the water a suitable adjuvant for adjusting the pH, for example, an acid adjuvant when the water is too alkaline. For most agricultural chemicals which are alkali sensitive or acid sensitive, the optimum or at least acceptable pH range for good agricultural activity of the chemical in question may be obtained from known references in the relevant art (for example, *The Agrochemicals Handbook*, Hartley, D. and Kidd, H. (Eds.), Royal Society of Chemistry, Nottingham, 1991) or such information may be provided by the manufacturer of the chemical in question.

To prepare an aqueous solution of a pH sensitive agricultural chemical, the pH of the water supply is first measured, and a suitable quantity of adjuvant is added to the water to obtain the desired pH. The user must accordingly be equipped with suitable equipment to test the pH of the water, and the pH of the resultant solution following addition and mixing of the agricultural chemical(s) to the water. Commonly used equipment for testing pH includes, for example, a pH meter and a pH indicator which provides visual colour changes indicative of pH range, such as pH sensitive paper (test strips) or chemicals. However, it is cumbersome and time consuming for the user to perform such operations while in the field. In addition, it may be uneconomical to carry pH testing equipment into the field as pH meters can be expensive, bulky and inconvenient, and pH test strips can degrade and become unreliable upon exposure to moisture or temperature extremes. Also, such pH determinations done in the field are often prone to human error. All of these issues can lead to significant wastage of the agricultural chemicals to be applied, as well as possible overuse and/or overexposure of crops, soil and animals to the agricultural chemicals. Accordingly, it is preferable to avoid such pH determinations or measurements during preparation of the aqueous solution of agricultural chemical(s) ("the agricultural composition") and to provide automatic identification of the desired pH or an acceptable pH during preparation of the agricultural composition.

Commonly used agricultural chemicals and compositions are known to have negative impacts on the environment. For example, phosphate-based compositions that run off into nearby waterways may cause eutrophication (over-fertilization) of aquatic ecosystems, which typically results in loss of oxygen from the water and concomitant loss of fish populations and other aquatic species. In addition, application of nitrogen- and/or phosphate-based agricultural compositions may cause fertilizer burn (leaf scorch), wherein plant tissues are exposed to localized high concentrations of the agricultural compositions. This causes hypertonicity and dessication of the exposed plant tissues, which results in crop damage and loss. At the same time, increasing public awareness of the negative impacts of such agricultural compositions on crop, soil and animal health, as well as the environment in general, have led consumers to turn increasingly towards agricultural products which are raised and labelled as "organic", such as crops that have been grown using a minimum of only fertilizers and pesticides that are known to be environmentally friendly, and animals that have been raised on such crops. This in turn has led the agricultural industry to seek out alternative agricultural chemicals that are more environmentally friendly. It is also desirable to find a means to increase the efficacy of existing agricultural compositions and thus reduce the total amount of chemicals applied.

Previously, agricultural compositions in concentrate form, comprising a visual pH indicator and a pH modifying agent, were disclosed in U.S. Pat. No. 5,278,132 and U.S. Pat. No. 5,514,639.

U.S. Pat. No. 5,278,132 disclosed a concentrate comprising a pH modifying agent and a pH indicator for colouring water, which concentrate may be diluted with water and added to a pH sensitive agricultural chemical, having an optimum activity within the range of pH 4-6. The proportions of the pH modifying agent and the pH indicator in the concentrate are such that when the concentrate is diluted to the appropriate concentration with water, and the pH of the resultant solution is modified by the pH modifying agent, the pH indicator indicates visually when the pH of the water is in the range of pH 4.

U.S. Pat. No. 5,514,639 disclosed a concentrate comprising a mixture of a pH indicator for colouring water, an agricultural chemical, and a pH modifying agent for modifying the pH of water with which the concentrate is diluted. The agricultural chemical has an activity that varies with the pH of the water and has an acceptable agricultural activity within a range of pH 4-6. The proportions of the pH modifying agent, the pH indicator and the agricultural chemical in the concentrate are such, that when the concentrate is diluted with an appropriate amount of water, an effective concentration of the agricultural chemical is provided and the pH indicator indicates visually when the pH of the solution is in the range of pH 4-6.

Although the compositions disclosed in both U.S. Pat. No. 5,278,132 and U.S. Pat. No. 5,514,639 provided a simple means for immediate visual identification of an aqueous solution of agricultural chemical being in the optimum pH range, in both cases the preferred pH modifying agent was a phosphate-based buffer system and the preferred pH indicator was methyl red, resorcin blue, 2,5-dinitrophenol and chlorophenol red. Examples of suitable phosphate buffer systems included phosphoric acid, and a conjugate base provided by any one of the following: monoammonium phosphate, potassium phosphate, monoorthophosporic esters and diorthophosphoric esters. However, it is not desirable to have a high concentration of phosphates present within agricultural compositions due to their ability to cause eutrophication and the associated negative impact on the environment. Also, agricultural compositions containing phosphoric acid and phosphates may cause leaf scorch which results in crop damage and loss. Inorganic phosphates and salts have also been found to lack compatibility and reduce the efficacy of a number of pesticides. For example, copper hydroxide-based fungicides lack compatibility with compositions containing phosphates. In the presence of phosphates, copper will form a water-insoluble salt, copper phosphate, which precipitates out of solution. As such, it is desirable to significantly reduce the concentration of phosphates in compositions for agricultural use.

A possible alternative to agricultural compositions containing high levels of phosphoric acid and phosphates could be provided by the use of one or more carbohydrate acid(s) as the pH modifying agent or as a component of the pH modifying agent of the concentrate in the place of an inorganic acid. The inclusion one or more carbohydrate acid(s) of could provide a number of advantages over agricultural compositions comprising phosphates and/or phosphoric acid. Carbohydrate acids typically have smaller dissociation constants ($K_a$) than phosphoric acid, and thus tend to be weaker acids than mineral acids such as phosphoric acids, which have large dissociation constants. As such, the inclusion of one or more carbohydrate acids in the pH modifying agent could result in a less harmful and corrosive composition. In addition, the presence of the carbohydrate moiety assists in the uptake of pesticides and nutrients in plants and soil microbes that have been treated with the agricultural composition. In addition, a carbohydrate-based pH modifying agent within the concentrate and the agricultural composition prepared from the concentrate could provide an additional nutrient source to treated plants and soil microbes. Carbohydrates are a compatible and effective source of organic nutrients for treated plants and soil microbes, particularly if micronutrients are present in the composition.

However, it has been surprisingly discovered that pH indicators previously used in agricultural compositions such as methyl red, resorcin blue, 2,5-dinitrophenol, chlorophenol red and anthocyanins have low stability when used in conjunction with carbohydrate acids in agricultural compositions and hence are not effective for indicating pH levels in such compositions. In fact, it has been determined that methyl red breaks down with the presence of carbohydrate acids in the agricultural compositions making the colour change ineffectual in a relatively short period of time, particularly when temperatures exceed thirty degrees Celsius.

Accordingly, there is a need for a means for simple and automatic identification of the desired pH during preparation of the agricultural composition, wherein such means is also environmentally friendly to crops, soil and animals. There is a need for such a composition that includes a carbohydrate acid in the pH modifying agent and a pH indicator that is compatible with carbohydrate acids.

SUMMARY OF THE INVENTION

In accordance with a broad aspect of the present invention there is provided a composition comprising:
a pH indicator for colouring an aqueous solution, wherein said pH indicator is a triarylmethane dye having a visible colour transition within the range of about pH 4 to about pH 6;
a pH modifying agent comprising one or more carbohydrate acids; and
optionally an agricultural chemical for application to crops, soil or animals, wherein said agricultural chemical has an activity that varies with the pH of the water and an acceptable agricultural activity at a pH within the range of about pH 4 to about pH 6;
wherein said composition is provided as a concentrate to be diluted with water, and wherein the proportions of the pH modifying agent and the pH indicator in the concentrate are such that when the concentrate is diluted with water and the pH of the water is modified by the pH modifying agent, the pH indicator indicates visually when the pH of the water is in the range of pH 4 to pH 6.

In an embodiment of the invention, the composition is a concentrate in the form of a liquid, a semi-liquid, gel and a paste. The composition may further comprise water.

In another embodiment of the invention, the concentrate comprises one or more carbohydrate acids selected from the group consisting of aldonic acids, uronic acids and aldaric acids. The carbohydrate acid may be selected from the group consisting of glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, erythronic acid, threonic acid, tartaric acid and any combination thereof.

In yet another embodiment of the invention, the composition further comprises an acid selected from the group consisting of acetic acid, orthophosphoric acid, citric acid, glutaric acid, glycolic acid, lactic acid, malonic acid, oxalic acid, phthalic acid, succinic acid, phosphorus acid, amino-tris(methylenephosphonic) acid, and etidronic acid.

In another embodiment of the invention, the composition further comprises a buffer system. The buffer system comprises a salt of a conjugate base of any acid present within the composition. Thus, in the case where the composition comprises a carbohydrate acid, the buffer system may comprise a salt of a conjugate base of the one or more carbohydrate acids present within the composition. In the case where the composition comprises an acid selected from the group consisting of acetic acid, orthophosphoric acid and citric acid, the buffer system may comprise a salt of a conjugate base of the acid that is selected. For example, the buffer system may comprise compounds selected the group consisting of phosphate salts such as monoammonium phosphate and monopotassium phosphate, acetate salts such as sodium acetate, citrate salts such as sodium citrate, and potassium hydrogen phthalate.

The pH modifying agent of the composition may further comprise an alkali.

In an embodiment of the invention, the pH indicator is selected from the group consisting of bromocresol green, bromocresol purple, bromophenol blue and chlorophenol red.

In another embodiment of the invention, the agricultural chemical is selected from the group consisting of pesticides, defoliants, desiccants and plant nutrients. The pesticide may be selected from the group consisting of insecticides, nematocides, fungicides, herbicides, molluscicides and rodenticides. Additionally, the pesticides may be selected from the group consisting of organophosphates, carbamates, benzimidazoles, dicarboximides, bipyridols, pyrethroids and chlorinated hydrocarbons. Suitable examples of pesticides include azinphos methyl, benomyl, captan, dimethoate, methomyl, trichlorfon, oxamyl, dibrom, dimecron, monocrotophos, diquat, cypermethrin, dicofol, acephate, acetamiprid, acrinathrin, aldicarb, amitraz, amitrole, azinphos methyl, bendiocarb, benfuresate, bensulfuron methyl, bentazone, 2,4-D, bitertanol, butamifos, butylate, cadusafos, captan, carbaryl, chinomethionat, chlorfenvinphos, chlorfluazuron, chlorimuron ethyl, chlormequat, chlorobenzilate, chlorpropham, chlorpyrifos, cinmethylin, clofentezine, copper terephthalate trihydrate, cyfluthrin, cyhalothlin, cyhexatin, cypermethrin, cyproconazole, cyromazine, caminozide, deltamethrin, demeton, dazinon, dicamba, dichlofluanid, dichlorvos, diclomezine, dicofol, diethofencarb, difenoconazole, difenzoquat, diflubenzuron, dimethipin, dimethoate, dimethylvinphos, edifenphos, esprocarb, ethiofencarb, ethofenprox, ethoprophos, ethoxyquin, etobenzanide, etrimfos, fenarimol, fenbutatin oxide, fenitrothion, fenobucarb, fenpyroximate, fensulfothion, fenthion, fenvalerate, flucythrinate, flufenoxuron, fluoroimide, flusilazole, flusulfamide, flutolanil, fluvalinate, fosetyl, fosthiazate, glufosinate, glyphosate and its water-soluble salts, halfenprox, hexaflumuron, hexythiazox, imazalil, imazosulfuron, imibenconazole, iminoctadine, inabenfide, inorganic bromide, iprodione, isophenphos, isoprocarb, lenacil, malathion, maleic hydrazide, 2-methyl-4-chlorophenoxyacetic acid (MCPA), MCPA-thioethyl, mepanipyrim, mephenacet, mepronil, methiocarb, methoprene, methoxychlor, metolachlor, metribuzin, mirex, myclobutanil, mitenpyram, oxamyl, paclobutrazol, pencycuron, pendimethalin, permethrin, phenthoate, phosalone, phoxim, picloram, pirimicarb, pirimiphos-methyl, pretilachlor, prohexadione, propamocarb, propiconazole, prothiofos, pyraclofos, pyrazoxyfen, pyrethrins, pyridaben, pyridate, pyrifenox, pyrimidifen, pyriproxyfen, quinalphos, quinclorac, sethoxydim, silafluofen, tebuconazole, tebufenozide, tebufenpyrad, tecloftalam, tefluthrin, terbufos, thenylchlor, thiobencarb, thiometon, tralomethrin, triadimenol, tribenuron methyl, trichlamide, trichlorfon, triclofos-methyl, tricyclazole, triflumizole, and vamidothion.

The composition as described in any of the above-noted embodiments may further comprise one or more additives selected from the group consisting of surfactants, spreading agents, wetting agents, emulsifiers, thickening and sticking agents, penetrating agents, humectants, dispersing agents, antifoaming agents, compatibility agents, micronutrients and preservatives.

In another broad aspect of the invention, there is provided a process for preparing an agricultural composition comprising an agricultural chemical with an activity which varies with the pH of the water and an acceptable agricultural activity at a pH within the range of about pH 4 to about pH 6, which is suitable for application to crops, soil or animals, comprising:
(a) providing a composition in concentrated form, comprising:
a pH indicator for colouring an aqueous solution, wherein said pH indicator is a triarylmethane dye having a visible colour transition within the range of about pH 4 to about pH 6;
a pH modifying agent comprising one or more carbohydrate acids;
wherein the proportions of the pH modifying agent and the pH indicator in the composition are selected so that when the concentrate is diluted with water to provide an effective concentration of pH modifying agent in the water, the pH indicator indicates visually whether or not the pH of the water is suitable for acceptable agricultural activity of the agricultural chemical; and
(b) preparing a solution by diluting said composition of step (a) with water so as to effect a colour change of the pH indicator that indicates that the pH of the composition of step (a) is in the range of about pH 4 to about pH 6; and
(c) adding the agricultural chemical to the solution of step (b) and mixing to form said agricultural composition.

In an embodiment of the above-noted process of the invention, the composition of step (a) comprises one or more carbohydrate acids selected from the group consisting of aldonic acids, uronic acids and aldaric acids. In a further embodiment, the carbohydrate acid may be selected from the group consisting of glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, erythronic acid, threonic acid, tartaric acid, glycolic acid and any combination thereof.

In addition, the composition of step (a), the pH modifying agent may further comprise an acid selected from the group consisting of acetic acid, orthophosphoric acid, citric acid, glutaric acid, glycolic acid, lactic acid, malonic acid, oxalic acid, phthalic acid, succinic acid, phosphorus acid, amino-tris (methylenephosphonic) acid, and etidronic acid.

In another embodiment of the above-noted process, the pH modifying agent may be prepared by an oxidation reaction of a reducing sugar. As such, the pH modifying agent may further comprise a mixture of said reducing sugar and one or more reaction products of said oxidation reaction.

In a further embodiment of the above-noted process of the invention, the pH modifying agent of the composition of step (a) further comprises a buffer system. The buffer system comprises a salt of a conjugate base of any acid present within the composition. Thus, in the case where the composition comprises a carbohydrate acid, the buffer system may comprise a salt of a conjugate base of the one or more carbohydrate acids present within the composition. In the case where the composition comprises an acid selected from the group consisting of acetic acid, orthophosphoric acid and citric acid, the buffer system may comprise a salt of a conjugate base of the acid that is selected. For example, the buffer system may comprise compounds selected from the group consisting of phosphate salts such as monoammonium phosphate and monopotassium phosphate, acetate salts such as sodium acetate, citrate salts such as sodium citrate, and potassium hydrogen phthalate.

In yet another embodiment of the above-noted process of the invention, in the composition of step (a), the pH indicator may be selected from the group consisting of bromocresol green, bromocresol purple, bromophenol blue and chlorophenol red. In addition, the agricultural chemical may be a compound selected from the group consisting of pesticides, defoliants, desiccants and plant nutrients.

In yet another broad aspect of the invention, there is provided a process for preparing an agricultural composition which is suitable for application to crops, soil or animals, comprising:
(a) providing a composition in concentrated form comprising:
a pH indicator for colouring an aqueous solution, wherein said pH indicator is a triarylmethane dye having a visible colour transition within the range of about pH 4 to about pH 6;
a pH modifying agent comprising one or more carbohydrate acids; and
an agricultural chemical for application to crops, soil or animals, wherein said agricultural chemical has an activity that varies with the pH of the water and an acceptable agricultural activity at a pH in the range of about pH 4 to about pH 6;

wherein the proportions of pH modifying agent, pH indicator and agricultural chemical in the composition in concentrated form are such that, when diluted with water to provide an effective concentration of the agricultural chemical and the pH of the water is modified by the pH modifying agent, the pH indicator indicates visually when the pH of the water is in the range of about pH 4 to about pH 6; and (b) diluting said composition of step (a) with water so as to effect a colour change of the pH indicator that indicates that the pH of the water is in the range of about pH 4 to about pH 6.

In an embodiment of the above-noted process of the invention, the composition of step (a) comprises one or more carbohydrate acids selected from the group consisting of aldonic acids, uronic acids and aldaric acids. In a further embodiment, the carbohydrate acid may be selected from the group consisting of glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, erythronic acid, threonic acid, tartaric acid, glycolic acid and any combination thereof.

In addition, the composition of step (a), the pH modifying agent may further comprise an acid selected from the group consisting of acetic acid, orthophosphoric acid, citric acid, glutaric acid, glycolic acid, lactic acid, malonic acid, oxalic acid, phthalic acid, succinic acid, phosphorus acid, amino-tris (methylenephosphonic) acid, and etidronic acid.

In another embodiment of the above-noted process, the pH modifying agent may be prepared by an oxidation reaction of a reducing sugar. As such, the pH modifying agent may further comprise a mixture of said reducing sugar and one or more reaction products of said oxidation reaction.

In a further embodiment of the above-noted process of the invention, the pH modifying agent of the composition of step (a) further comprises a buffer system. The buffer system comprises a salt of a conjugate base of any acid present within the composition. Thus, in the case where the composition comprises a carbohydrate acid, the buffer system may comprise a salt of a conjugate base of the one or more carbohydrate acids present within the composition. In the case where the composition comprises an acid selected from the group consisting of acetic acid, orthophosphoric acid and citric acid, the buffer system may comprise a salt of a conjugate base of the acid that is selected. For example, the buffer system may comprise compounds selected from the group consisting of phosphate salts such as monoammonium phosphate and monopotassium phosphate, acetate salts such as sodium acetate, citrate salts such as sodium citrate, and potassium hydrogen phthalate.

In yet another embodiment of the above-noted process of the invention, in the composition of step (a), the pH indicator may be selected from the group consisting of bromocresol green, bromocresol purple, bromophenol blue and chlorophenol red. In addition, the agricultural chemical may be a compound selected from the group consisting of pesticides, defoliants, desiccants and plant nutrients.

An advantage of the invention is that it provides a simple, rapid and accurate method of making and/or maintaining an aqueous agricultural chemical composition at its optimum pH range. A number of agricultural chemicals may be degraded by exposure to extremes in pH or exhibit lowered activity in the presence of non-optimum pH levels. The invention thus aids in stabilizing the agricultural chemical and promoting optimal efficacy of the agricultural chemical with either an alkaline or acidic water supply. Moreover, the user, operator or other field staff is saved the necessity of calculating the precise amount of pH modifying agent to be added to the composition, and need not be skilled in pH measurement or require pH measuring equipment that requires training to use. That is, the user need not be skilled or highly trained to operate the invention. The invention also aids in reducing wastage of agricultural chemicals by significantly reducing opportunities for human error during preparation of the agricultural composition.

Another advantage of the invention is that it provides a simple, rapid and accurate method of preparing an agricultural composition comprising one or more agricultural chemicals at the appropriate concentration and at the optimum pH range for optimal agricultural activity.

Yet another advantage of the invention is that the concentrate comprises a carbohydrate-based pH modifying agent. The inclusion of one or more carbohydrate acid(s) in the pH modifying agent of the concentrate provides a number of advantages over agricultural compositions comprising phosphates and/or phosphoric acid. Carbohydrate acids typically have smaller dissociation constants ($K_a$) than phosphoric acid, and thus tend to be weaker acids than mineral acids such as phosphoric acids, which have large dissociation constants. As such, the inclusion of one or more carbohydrate acids in the pH modifying agent results in a less harmful and corrosive composition. Agricultural compositions comprising phosphates and/or phosphoric acid can cause leaf scorch in treated plants, and localized "burns" on treated animals, whereas agricultural compositions comprising carbohydrate acids do not cause such damage. As such, the agricultural composition prepared from the concentrate of the invention is gentler to treated plants, soil microbes and animals. It is also safer for human users and plant/animal life that may be exposed to the concentrate and the agricultural composition prepared from the concentrate. In addition, the presence of the carbohydrate moiety assists in the uptake of pesticides and nutrients in plants and soil microbes that have been treated with the agricultural composition.

Yet another advantage of the invention is that the inclusion of one or more carbohydrate acids in the pH modifying agent allows for increased compatibility of the concentrate and the agricultural composition with common micronutrient additives such as copper, magnesium and zinc. In comparison, concentrates and agricultural compositions comprising a relatively high concentration of phosphates and/or orthophosphoric acid typically exhibit lower compatibility with micronutrients such as copper, magnesium and zinc, as these metals tend to form insoluble salts with the phosphates. These insoluble salts then precipitate out of solution, and thus are no longer available to provide nutritive value.

Another advantage of the invention is that the presence of the carbohydrate-based pH modifying agent within the concentrate and the agricultural composition prepared from the concentrate provides an additional nutrient source to treated plants and soil microbes. Carbohydrates are a compatible and effective source of organic nutrients for treated plants and soil microbes, particularly if micronutrients are present in the composition Other and further advantages and features of the invention will be apparent to those skilled in the art from the following detailed description of an embodiment thereof.

DETAILED DESCRIPTION OF EMBODIMENTS

The objective was to prepare a concentrate for use in preparation of an agricultural composition, wherein the concentrate provides a means for simple and automatic identification of the desired or an acceptable pH during preparation of the agricultural composition, and such means is also environmentally friendly to crops, soil and animals. The purpose of the concentrate is to adjust the pH, and optionally buffer the pH, of the agricultural composition to a pH which is the optimum pH of any given agricultural chemical to be included in the composition, and to provide the user with a visible colouration of the agricultural solution which is indicative of the optimum pH. As such, the concentrate comprises a pH modifying agent, a pH indicator, and optionally, one or more agricultural chemicals. Upon addition of an appropriate amount of water to form a solution, the concentrate would indicate, by visual colour change or appropriate colouration of the resultant solution, whether the pH of the solution was in the appropriate range of about pH 4 to about pH 6.

It was thought that a pH modifying agent based on an organic acid may overcome the problems associated with phosphate use in agricultural compositions such as the compositions described in U.S. Pat. No. 5,278,132 and U.S. Pat. No. 5,514,639. Organic acids tend to be weaker acids than mineral acids such as phosphoric acids, which are typically strong acids. As such, it was thought that a pH modifying agent based on an organic acid would be less harmful to plant tissues and may also assist in the uptake of pesticides and nutrients. At the same time, it is well documented that the use of carbohydrates aids in the uptake of various nutrients or pesticides by the plant.

It has now been found that a composition comprising a pH indicator comprising a triarylmethane dye, and an organic acid derived from a carbohydrate, provides a number of unexpected and advantageous characteristics that are useful for preparation of aqueous solutions of agricultural chemicals (referred to in general as "agricultural compositions"). The composition comprising the pH indicator and the organic acid derived from a carbohydrate is preferably provided in concentrated form and thus is also referred to herein as "the concentrate". The concentrate may then be diluted with water in the preparation of an agricultural composition for application to crops, soil or animals. The proportions of pH modifying agent and pH indicator in the concentrate are selected such that when the concentrate is diluted with the appropriate amount of water, the pH indicator indicates visually whether or not the pH of the water is suitable for acceptable activity of the agricultural chemical in question.

As noted above, the concentrate comprises a pH modifying agent selected from the group comprising acids, alkalis and buffers for controlling and modifying the pH of water.

For use in areas where the available water, such as ground/borehole water or river water is alkaline, the pH modifying agent may be an acid. If the available water supply is too acidic, an alkaline pH modifying agent may be employed, for example, a member of the group comprising ammonia, potassium hydroxide and sodium hydroxide.

Organic acids may be prepared by oxidation of a carbohydrate bearing at least one primary alcohol moiety (—OH) and/or one aldehyde moiety. Such carbohydrate-based organic acids are referred to herein as "carbohydrate acids". Preparation of organic acids by oxidation of primary alcohols and aldehydes is well known in the art (see for example, Loudon, G. M., *Organic Chemistry* 5$^{th}$ ed., Roberts & Co., 2009); other methods of preparing organic acids are also well known in the art. For example, oxidation of aldehydes to form the corresponding carboxylic acid may be carried out with potassium permanganate ($KMnO_4$), chromium (VI) reagents or nitric acid ($HNO_3$) (see for example, Bose. R. et al. "Iso-lation of 1,4- and 6,3-lactones of D-glucaric acid", *Journal of Organic Chemistry*, 1961, 26(4), pp. 1300-1301).

Suitable carbohydrates for preparing carbohydrate acids include "reducing sugars", which refers to any sugar that, in aqueous solution, may exist in an open chain form with a free aldehyde and/or ketone moiety (see for example, De Lederkremer, R. M. and Marino, C., *Advances. Carb. Chem. Biochem.*, 2003, 58, 199). Those monosaccharides that belong to this group of reducing sugars may also be referred to as "reducing monosaccharides". Reducing monosaccharides which contain an aldehyde group are referred to as aldoses, and those with a ketone group are referred to as ketoses. Non-limiting examples of reducing monosaccharides include glyceraldehyde, erythrose, threose, ribose, arabinose, xylose, lyxose, allose, altrose, glucose, mannose, gulose, idose, galactose, talose, erythrulose, ribulose, xylulose, psicose, fructose, sorbose and tagatose. Non-limiting examples of reducing disaccharides include sucrose, maltose, cellobiose, trehalose, isomaltose, lactose, lactulose and the oligosaccharides, xylo-, fuco-, manno-, galacto- and gluco-oligosaccharides.

Polysaccharides may also be used to prepare carbohydrate acids. Non-limiting examples of polysaccharides that may be used to prepare carbohydrate acids include starch and cellulose, and various polysaccharides derived from biomass, plant and/or microorganism sources.

Oxidation of sugars yields carbohydrate acids generally referred to as "sugar acids"; the oxidation of aldoses yields aldonic acids, uronic acids (wherein the terminal hydroxyl group has been oxidized to a carboxylic acid group) and aldaric acids (wherein both the terminal hydroxyl group and the aldehyde group at Cl have been fully oxidized to carboxylic acid groups). See for example, Robyt, J. F., *Essentials of Carbohydrate Chemistry*, New York: Springer, 1998. Carbohydrate acids may also be obtained by epimerization of other carbohydrate acids.

Oxidation of one or more carbohydrate acids by the above-noted methods may result in a mixture of compounds, which comprises the starting compound(s) (i.e. the carbohydrate, which may be a reducing sugar such as an aldose, ketose, disaccharide, or a polysaccharide such as a starch), partially oxidized forms of the starting compound(s) and the fully oxidized carbohydrate acid(s). Such a mixture is also suitable for use as a component of the pH modifying agent in the concentrate.

In a preferred embodiment, the concentrate comprises a carbohydrate acid. In yet another embodiment, the carbohydrate acid is prepared by oxidation of reducing sugars such as glucose, fructose, galactose, mannose, ribose, arabinose, xylose, erythrose, threose and glyceraldehyde. Suitable non-limiting examples of carbohydrate acids that may be used include glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, erythronic acid, threonic acid, tartaric acid, glycolic acid and any combination thereof.

In another preferred embodiment, the concentrate comprises a buffer system based on one or more carbohydrate acids and the appropriate conjugate base(s), typically present as the salt of the conjugate base. Suitable, non-limiting examples of salts include Group I and Group II metal salts of the corresponding carbohydrate acid. For example, a typical buffer system may comprise glucoheptonic acid and sodium glucoheptonate. Persons skilled in the relevant art will appreciate that numerous combinations of carbohydrate acids and salts of carbohydrate acids can be employed as a buffer system, and suitable buffer systems may be arrived at without difficulty and by routine experimentation. Should the user happen to dilute the concentrate with an incorrect amount of water, the buffer serves to guard against excessive pH modification and extremes in pH.

In yet another embodiment of the invention, the concentrate further comprises one or more other acids as part of the pH modifying agent. Non-limiting examples include acetic acid, orthophosphoric acid, citric acid, glutaric acid, glycolic acid, lactic acid, malonic acid, oxalic acid, phthalic acid, succinic acid, phosphorus acid, amino-tris(methylenephosphonic) acid, and etidronic acid. In such a case, the concentrate may further comprise the salt(s) of the conjugate base(s) of the selected acid(s), in order to form an appropriate buffer system.

As many agricultural chemicals typically have an optimum activity in a slightly acidic pH range (for example, pH 4-6), the concentrate comprises a suitable pH indicator that is one of the known triarylmethane dyes which exhibits a visible colour change in the range of pH 4 to pH 6. Thus, suitable triarylmethane pH indicators with appropriate pH colour transitions in the range of pH 4-6 are as follows:

| pH Indicator | Range of pH colour transition | Colour change (from lower pH to higher pH) |
| --- | --- | --- |
| bromophenol blue | pH 3.0-4.6 | yellow/purple |
| bromocresol green | pH 3.8-5.4 | yellow/blue |
| chlorophenol red | pH 4.8-6.7 | yellow/violet |
| bromocresol purple | pH 5.2-6.8 | yellow/purple |

In an embodiment, the concentrate comprises bromocresol green. In yet another embodiment, the concentrate comprises bromocresol blue. In yet another embodiment, the concentrate comprises bromophenol purple. In another embodiment, the concentrate comprises chlorophenol red.

In an embodiment, the concentrate is in liquid, semi-liquid, gel or paste form. Such forms facilitate handling and measurement of the concentrate by the user in the field. The concentrate may comprise water to further facilitate handling and measurement of the concentrate and to dissolve or disperse various ingredients therein, as well as to aid in dispersion of the concentrate during dilution with water.

The concentrate may further comprise one or more agricultural chemical(s) whose agricultural activity varies with the pH of water with which it is in contact and whose agricultural activity is acceptable in the pH range to which the buffer buffers water to which it is added. Admixing of this concentrate with water will automatically, within limits, show whether or not the resultant aqueous solution is within an acceptable pH range, due to the colouration of the water by the pH indicator that is present within the concentrate.

The agricultural chemical may be selected from the group comprising pesticides, defoliants, desiccants, and plant nutrients. The agricultural chemical may be a pesticide, selected from the group consisting of insecticides, nematocides, fungicides, herbicides, molluscicides and rodenticides. More particularly, the agricultural chemical may be selected from the group comprising organophosphates, carbamates, benzimidazoles dicarboxamides, bipyridols, pyrethroids and chlorinated hydrocarbons. Suitable non-limiting examples of agricultural chemicals that may be selected include azinphos methyl, benomyl, captan, dimethoate, methomyl, trichlorfon, oxamyl, dibrom, dimecron, monocrotophos, diquat, cypermethrin, dicofol, acephate, acetamiprid, acrinathrin, aldicarb, amitraz, amitrole, azinphos methyl, bendiocarb, benfuresate, bensulfuron methyl, bentazone, 2,4-D, bitertanol, butamifos, butylate, cadusafos, captan, carbaryl, chinomethionat, chlorfenvinphos, chlorfluazuron, chlorimuron ethyl, chlormequat, chlorobenzilate, chlorpropham, chlorpyrifos, cinmethylin, clofentezine, copper terephthalate trihydrate, cyfluthrin, cyhalothlin, cyhexatin, cypermethrin, cyproconazole, cyromazine, caminozide, deltamethrin, demeton, dazinon, dicamba, dichlofluanid, dichlorvos, diclomezine, dicofol, diethofencarb, difenoconazole, difenzoquat, diflubenzuron, dimethipin, dimethoate, dimethylvinphos, edifenphos, esprocarb, ethiofencarb, ethofenprox, ethoprophos, ethoxyquin, etobenzanide, etrimfos, fenarimol, fenbutatin oxide, fenitrothion, fenobucarb, fenpyroximate, fensulfothion, fenthion, fenvalerate, flucythrinate, flufenoxuron, fluoroimide, flusilazole, flusulfamide, flutolanil, fluvalinate, fosetyl, fosthiazate, glufosinate, glyphosate and its water-soluble salts, halfenprox, hexaflumuron, hexythiazox, imazalil, imazosulfuron, imibenconazole, iminoctadine, inabenfide, inorganic bromide, iprodione, isophenphos, isoprocarb, lenacil, malathion, maleic hydrazide, 2-methyl-4-chlorophenoxyacetic acid (MCPA), MCPA-thioethyl, mepanipyrim, mephenacet, mepronil, methiocarb, methoprene, methoxychlor, metolachlor, metribuzin, mirex, myclobutanil, mitenpyram, oxamyl, paclobutrazol, pencycuron, pendimethalin, permethrin, phenthoate, phosalone, phoxim, picloram, pirimicarb, pirimiphos-methyl, pretilachlor, prohexadione, propamocarb, propiconazole, prothiofos, pyraclofos, pyrazoxyfen, pyrethrins, pyridaben, pyridate, pyrifenox, pyrimidifen, pyriproxyfen, quinalphos, quinclorac, sethoxydim, silafluofen, tebuconazole, tebufenozide, tebufenpyrad, tecloftalam, tefluthrin, terbufos, thenylchlor, thiobencarb, thiometon, tralomethrin, triadimenol, tribenuron methyl, trichlamide, trichlorfon, triclofos-methyl, tricyclazole, triflumizole, and vamidothion.

If the concentrate further comprises an agricultural chemical, the pH indicator and the pH modifying agent that are selected for inclusion in the concentrate are compatible or inert with regards to the other constituents of the concentrate, in particular the agricultural chemical in the concentrate.

It will be known from standard references well known in the art (for example, *The Agrochemicals Handbook*, Hartley, D. and Kidd, H. (Eds.), Royal Society of Chemistry, Nottingham: 1991) or from the manufacturer's specifications, what concentration of agricultural chemical is necessary to be effective upon application to crops, soil or animals. The proportion of pH indicator in the concentrate will accordingly be related to the proportion or concentration of agricultural chemical present so that, when an appropriate amount of concentrate is added to water in preparing the agricultural composition to provide the intended concentration of agricultural chemical, the composition will automatically contain a sufficient proportion of pH indicator for easy visual pH determination. The pH indicator in turn will be chosen so that it can indicate, e.g. by undergoing a colour change or by having a distinctive colour at a suitable pH, when the desired or an acceptable pH has been attained. The user accordingly may simply add the appropriate or prescribed amount of the concentrate to the water, and, thereafter, add amounts of water or concentrate until the colour change takes place, or the appropriate colour is attained.

The concentrate may further comprise additives that provide additional performance characteristics that may be considered desirable by the user or operator. Such additives include, but are not limited to, surfactants, spreading agents, wetting agents, emulsifiers, thickening and sticking agents, penetrating agents, humectants, dispersing agents, antifoaming agents, compatibility agents, micronutrients and preservatives, and other additives typically employed when the eventual agricultural composition is intended for foliar application, or spraying/dipping animals.

In an embodiment, there is provided a process for preparing an aqueous agricultural composition for application to crops, soil or animals, and which contains an agricultural chemical whose agricultural activity varies with the pH of water with which it is in contact, the process comprising admixing, with the water, a concentrate as described above and the agricultural chemical and effecting such pH modification to the resultant composition as is necessary to obtain a pH in the composition at which said agricultural activity is acceptable.

In an embodiment of the above-noted process, the concentrate comprises a pH indicator and a pH modifying agent, both components as described above. Addition of the concentrate to the mixture acts to modify the pH of the composition. The agricultural chemical is then added separately and subsequently to the addition of the concentrate. In a preferred embodiment, any pH modification should take place before the agricultural chemical is added to a solution of water and the concentrate. This prevents degradation of the agricultural chemical prior to modification of the pH, and avoids any masking of the colour due to the pH indicator by the agricultural chemical.

In yet another embodiment of the above-noted process, the above-noted concentrate further comprises the agricultural chemical, so that adding the appropriate amount of water to the concentrate provides an agriculturally effective concentration of said chemical in the resultant agricultural composition. In addition, the resultant agricultural composition is at an acceptable pH level for optimum activity of the agricultural chemical, as indicated by the appropriate colouration of the agricultural composition, the colouration provided by the pH indicator.

Where the concentrate contains a buffer system as the pH modifying agent, a pH indicator as described above, and an agricultural chemical whose agricultural activity varies with the pH of water with which it is in contact, and whose agricultural activity is acceptable in the pH range to which the buffer system buffers water to which it is added, the concentrate may merely be admixed into the appropriate amount of water to prepare the intended agricultural composition. When the concentrate has been added to water in proportions sufficient to provide it with the intended agricultural activity, sufficient buffer will simultaneously and automatically be added to buffer the water to the appropriate pH range, and sufficient pH indicator will automatically be added to confirm that the water is in this pH range. The proportions of pH indicator and buffer will thus be set in the concentrate bearing these requirements in mind and bearing in mind the nature of the agricultural chemical in the concentrate. In this case, it is contemplated that, only with available waters of extremely high or extremely low pH ranges, will the buffer be unable to buffer the water to the appropriate pH range for good agricultural activity of the agricultural chemical, and in these exceptional cases the pH indicator will indicate that suitable buffering has failed to take place.

It will be appreciated that the embodiments of the invention are applicable to a large number of various different agricultural chemicals and that the concentrations of these chemicals can vary substantially in the eventual formulated agricultural composition for application to crops, soil or animals, depending, inter alia, on the nature of the agricultural chemical itself, the purpose for which it is being used, climatic conditions, the half-life of the agricultural chemical in water of a particular pH, frequency of application, the type of crop, environmental factors and economics, or the like. Furthermore, the concentration and rate at which these chemicals are applied may vary depending on crop and method of application. In each case, the proportion of pH indicator included in the concentrate will be related to the amount of water to be used for dilution of the concentrate, irrespective of the proportion of agricultural chemical therein. That is, sufficient pH indicator should be present when the concentrate has been added to water in the appropriate or intended dilution for the agricultural chemical, so that the pH indicator will be effective and visible at its appropriate dilution in the water. For the manufacturer of the concentrate, who will be aware of its intended use and who will prescribe the concentrations at which it will be used, it will be a simple matter to ensure that the concentrate contains sufficient pH indicator to be effective when the concentrate is used at these prescribed concentrations. Considerable and possibly radical variations in the proportions between the agricultural chemical and pH indicator in the concentrate are thus contemplated, and the absolute concentrations of the agricultural chemical and pH indicator in the concentrate can also vary radically. It has been found, however, that no difficulty is presented in determining such absolute concentrations and relative concentrations, by means of routine experimentation. The proportion of pH indicator present in the concentrate may thus vary considerably from one concentrate to another, depending on how much of the concentrate is intended to be added to water. Similar considerations apply when the concentrate comprises a pH indicator and a pH modifying agent, and the agricultural chemical is added separately to form the agricultural composition.

Further details of the preferred embodiments of the invention are illustrated in the following Examples which are understood to be non-limiting with respect to the appended claims.

EXAMPLE 1

Preparation of Agricultural Concentrate Based on Carbohydrate Acid and Previously Known pH Indicators The objective was to prepare a concentrate for use in preparation of an agricultural composition, wherein the purpose of the concentrate is to adjust the pH, and optionally buffer the pH, of the agricultural composition to a pH which is the optimum pH of any given agricultural chemical to be included in the composition, and to provide the user with a visible colouration of the agricultural solution which is indicative of the optimum pH. As such, the concentrate would comprise a pH modifying agent, a pH indicator, and optionally, one or more agricultural chemicals.

Many agricultural chemicals have an optimum activity in the range of about pH 4 to about pH 6. Upon addition of an appropriate amount of water to form a solution, the concentrate would indicate, by visual colour change or appropriate colouration of the resultant solution, whether the pH of the solution was in the appropriate range of about pH 4 to about pH 6. An organic acid was included as part of the pH modifying agent to reduce the dependency on phosphoric acids as the main pH modifying agent.

Carbohydrate acid mixtures were prepared by nitric acid oxidation of starch (Bose. R. et al. "Isolation of 1,4- and 6,3-lactones of D-glucaric acid", *Journal of Organic Chemistry*, 1961, 26(4), pp. 1300-1301). As noted above, oxidation of a carbohydrate acid by the above-noted methods may result in a mixture of compounds, which comprises the starting compound (i.e. the carbohydrate, which may be a reducing sugar such as an aldose, ketose, disaccharide, or a polysaccharide such as a starch), partially oxidized forms of the starting compound and the fully oxidized carbohydrate acid. Such a mixture was deemed suitable for use as a component of the pH modifying agent in the concentrate.

Anthocyanins are plant pigments that may appear red, purple or blue, depending on the pH of the solution in which they reside. Anthocyanins, such as those extracted from red cabbage leaves, may be used as a pH indicator, appearing in solution as red at pH less than 3, colourless at pH 4-5, violet at pH 6-7, blue at pH 7-8, and yellow at pH greater than 8. It was thought that a pH indicator based on plant-derived compounds may be useful in preparing an agricultural composition that is more environmentally friendly and gentler on plant and animal tissues to which the agricultural composition may be applied.

Agricultural concentrates comprising a pH modifying agent based on an carbohydrate acid derived from an aldose or a ketose, and a pH indicator, chosen from either methyl red (as disclosed in U.S. Pat. No. 5,278,132 and U.S. Pat. No. 5,514,639) or an anthocyanin-based compound were prepared. For example, concentrates containing 10-30 wt % phosphoric acid and esters and 10-30 wt % carbohydrate acid mixture with 0.1-0.5 wt % methyl red or 10-25 wt % cabbage extract were evaluated.

The concentrate samples were then stored at elevated temperatures to observe any changes in composition that would indicate problems with storage stability. It was found that the stability of the above-noted concentrates was negatively affected by fluctuations in storage temperature and/or prolonged storage time. It was found that at a storage temperature of about 40° C., a concentrate comprising a carbohydrate acid, and methyl red or an anthocyanin-based compound would deteriorate within about 3 to 4 weeks of storage. When stored at around 60° C., the concentrates would deteriorate within about 24 hours to 7 days.

It was found that the presence of the carbohydrate acid mixture, as the pH modifying agent, was responsible for the decomposition of the pH indicator, rendering the concentrate ineffective. In particular, poor stability was noted when either methyl red or anthocyanin-based colour indicators were used as the pH indicator.

EXAMPLE 2

Preparation of Agricultural Concentrate Based on Carbohydrate Acid and Bromocresol Green A series of concentrated compositions ("concentrates") for use in preparing an agricultural composition were prepared. The compositions of the concentrates are as provided in Table 2. In each case, the concentrate comprised (1) a mixture of reducing sugars and carbohydrate acids as a pH modifying agent and (2) a triarylmethane dye (in this case, bromophenol green) as the pH indicator. The mixture of reducing sugars and carbohydrate acids was prepared as noted above in Example 1, i.e. by oxidation of one or more reducing sugars with nitric acid (Bose. R. et al. "Isolation of 1,4- and 6,3-lactones of D-glucaric acid", *Journal of Organic Chemistry*, 1961, 26(4), pp. 1300-1301).

TABLE 2

Concentrated compositions ("Concentrates") for use in preparing an agricultural composition, comprising carbohydrate acids as a pH modifying agent and a triarylmethane dye as pH indicator.

| Ingredient | Amount (weight %) |
|---|---|
| (a) | |
| Alcohol ethoxylate | 14 |
| Carbohydrate acids | 40 |
| Bromocresol green | 2.8 |
| Water | 43.2 |
| Total | 100.0 |
| (b) | |
| Alcohol ethoxylate | 14 |
| Citric acid | 15 |
| Carbohydrate acids | 25 |
| Bromocresol green | 2.8 |
| Water | 43.2 |
| Total | 100.0 |
| (c) | |
| Alcohol ethoxylate | 14 |
| Phosphoric acid and esters | 20 |
| Carbohydrate acids | 20 |
| Bromocresol green | 2.8 |
| Water | 43.2 |
| Total | 100.0 |
| (d) | |
| Alcohol ethoxylate | 14 |
| Phosphoric acid and esters | 15 |
| Carbohydrate acids | 25 |
| Manganese sulphate monohydrate | 1 |
| Zinc sulfate | 8 |
| Iron sulphate heptahydrate | 3 |
| Bromocresol green | 2.8 |
| Water | 31.2 |
| Total | 100.0 |

Surprisingly, it was found that pH indicators from the group of triarylmethane dyes, such as bromocresol green, were stable in the presence of the carbohydrate acid mixtures. Thus, the compositions were stable to storage at elevated temperatures, i.e. at around 40° C. and at around 60° C. The concentrates noted in Table 2 and similar formulations were found to be stable when stored for more than 2 months at around 40° C., and stable for at least 4 weeks when stored at around 60° C.

In the above-noted composition, typical examples of carbohydrate acids that may be used as pH modifying agents include, but are not limited to: glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, erythronic acid, threonic acid, tartaric acid, glycolic acid and any combination thereof.

Other surfactants, spreading agents, wetting agents, emulsifiers, thickening and sticking agents, penetrating agents, humectants, dispersing agents, antifoaming agents, compatibility agents, micronutrients and preservatives, and other additives typically employed when the eventual agricultural composition is intended for foliar application, or spraying/dipping animals may be included in any one of the concentrates as provided in Tables 2 (a) to (d).

Numerous modifications, variations and adaptations may be made to the particular embodiments of the invention described above without departing from the scope of the invention, which is defined in the following claims.

We claim:
1. A composition comprising:
a pH indicator for colouring an aqueous solution, wherein said pH indicator is bromocresol green, bromocresol purple or bromocresol blue; and;
a pH modifying agent comprising one or more carbohydrate acids; and
optionally an agricultural chemical for application to crops, soil or animals, wherein said agricultural chemical has an activity that varies with the pH of the water and an acceptable agricultural activity at a pH within the range of about pH 4 to about pH 6;
wherein said composition is provided as a concentrate to be diluted with water, and wherein the proportions of the pH modifying agent and the pH indicator in the concentrate are such that when the concentrate is diluted with water and the pH of the water is modified by the pH modifying agent, the pH indicator indicates visually when the pH of the water is in the range of pH 4 to pH 6; and the composition is stable when stored for more than 4 months at about 40° C.

2. The composition according to claim 1, wherein said composition is in a form selected from the group consisting of a liquid, a semi-liquid, gel and a paste.

3. The composition according to claim 1, wherein said composition further comprises water.

4. The composition according to claim 1, wherein said one or more carbohydrate acids is selected from the group consisting of aldonic acids, uronic acids and aldaric acids.

5. The composition according to claim 4, wherein said carbohydrate acid is selected from the group consisting of glucoheptonic acid, gluconic acid, glucuronic acid, glucaric acid, mannonic acid, mannuronic acid, mannaric acid, galactonic acid, galactaric acid, galacturonic acid, guluronic acid, iduronic acid, ribonic acid, arabonic acid, xylonic acid, erythronic acid, threonic acid, tartaric acid, glycolic acid and any combination thereof.

6. The composition according to claim 1, wherein said pH modifying agent further comprises a buffer system.

7. The composition according to claim 6 wherein said buffer system comprises a salt of a conjugate base of the one or more carbohydrate acids present therein.

8. The composition according to claim 1, wherein said pH modifying agent further comprises an acid selected from the group consisting of acetic acid, orthophosphoric acid, citric acid, glutaric acid, glycolic acid, lactic acid, malonic acid, oxalic acid, phthalic acid, succinic acid, phosphorus acid, amino-tris(methylenephosphonic) acid, and etidronic acid.

9. The composition according to claim 8, wherein said buffer system comprises a salt of a conjugate base of the selected acid.

10. The composition according to claim 1, wherein said pH modifying agent further comprises an alkali.

11. The composition according to claim 1, wherein said agricultural chemical is selected from the group consisting of pesticides, defoliants, desiccants and plant nutrients.

12. The composition according to claim 11, wherein said agricultural chemical is a pesticide selected from the group consisting of insecticides, nematocides, fungicides, herbicides, molluscicides and rodenticides.

13. The composition according to claim 12, in which the agricultural chemical is a compound selected from the group consisting of organophosphates, carbamates, benzimidazoles, dicarboximides, bipyridols, pyrethroids and chlorinated hydrocarbons.

14. The composition according to claim 1, further comprising one or more additives selected from the group consisting of surfactants, spreading agents, wetting agents, emulsifiers, thickening and sticking agents, penetrating agents, humectants, dispersing agents, antifoaming agents, compatibility agents, micronutrients and preservatives.

15. A composition comprising:
2.8% by weight of the composition of a pH indicator for coloring an aqueous solution, wherein said pH indicator is bromocresol green; and
25% by weight of the composition of a pH modifying agent comprising one or more carbohydrate acids;
14% by weight of the composition of alcohol ethoxylate; and
43.2% by weight of the composition of water,
wherein said composition is provided as a concentrate to be diluted with water, and wherein the proportions of the pH modifying agent and the pH indicator in the concentrate are such that when the concentrate is diluted with water and the pH of the water is modified by the pH modifying agent, the pH indicator indicates visually when the pH of the water is in the range of pH 4 to pH 6; and the composition is stable when stored for more than 4 months at about 40° C.

* * * * *